United States Patent [19]

Klatt

[11] Patent Number: 4,597,765

[45] Date of Patent: Jul. 1, 1986

[54] METHOD AND APPARATUS FOR PACKAGING A FLUID CONTAINING PROSTHESIS

[75] Inventor: William M. Klatt, St. Louis Park, Minn.

[73] Assignee: American Medical Systems, Inc., Minnetonka, Mich.

[21] Appl. No.: 686,644

[22] Filed: Dec. 27, 1984

[51] Int. Cl.$^4$ ............................................... A61F 2/02
[52] U.S. Cl. ........................................ 623/11; 128/79; 206/63.3
[58] Field of Search ...................... 206/63.3, 438, 210, 206/570, 5.1; 3/1, 36; 604/895; 128/79

[56] References Cited

U.S. PATENT DOCUMENTS 3,202,273  8/1965  Riall .................................... 206/63.3
4,157,085  6/1979  Austed ...................................... 3/36
4,415,076  11/1983 Campbell ............................. 206/5.1

Primary Examiner—Richard J. Apley
Assistant Examiner—James Prizant
Attorney, Agent, or Firm—Arnold, White & Durkee

[57] ABSTRACT

A method and apparatus for packaging a fluid containing prosthesis adapted to be implanted in a sterile condition involves filling a closable, permeable fluid containing housing within the prosthetic device with a fluid. The prosthetic device is then enclosed within a substantially fluid impenetrable enclosure that is filled with a fluid with activities which substantially match the activities of the fluid within the prosthetic device. Thus, even where the prosthetic device contains a physiological solution, by incorporating a solution of equal solute concentration within the enclosure that surrounds the prosthetic device, the tendency for osmosis to occur across the barrier defined by the walls of the prosthetic device can be adequately controlled. The enclosure may then be enclosed within an outer bag which may be handled by a non-sterile nurse, preparatory to implantation by a surgeon. In this way, it is possible to ship a prosthetic device in a fluid filled state despite the tendency for migration through the walls of the device by establishing mass transfer equilibrium within the package.

24 Claims, 2 Drawing Figures

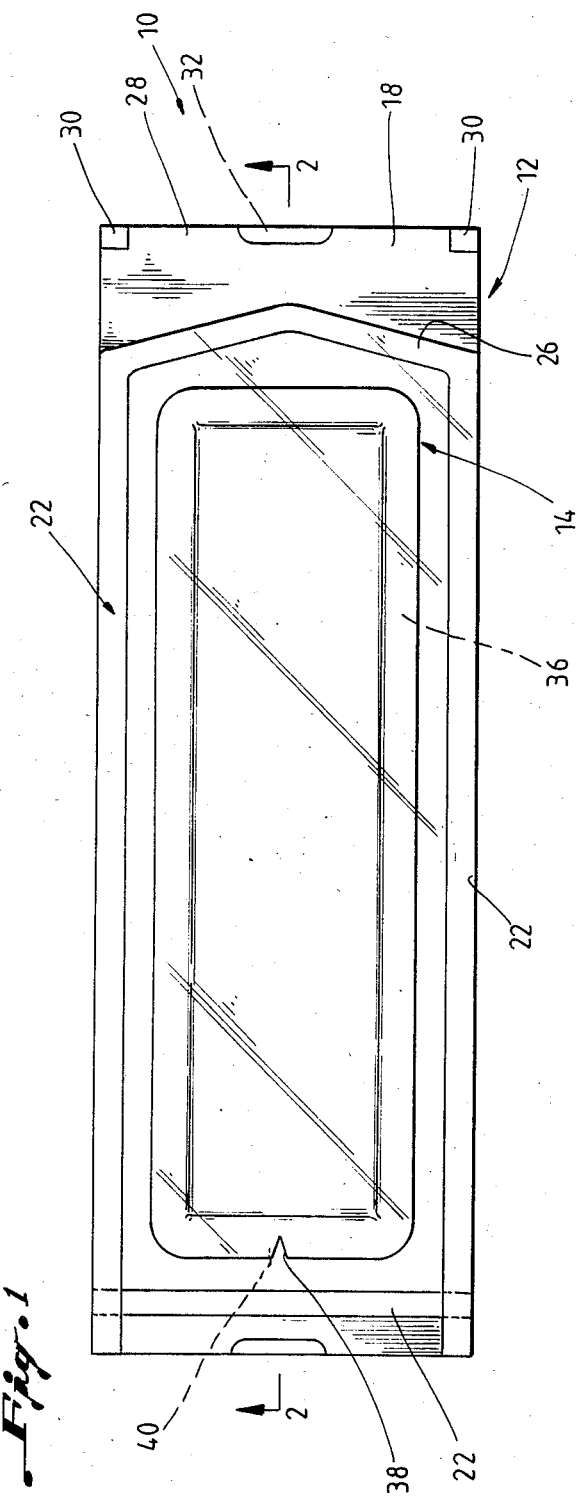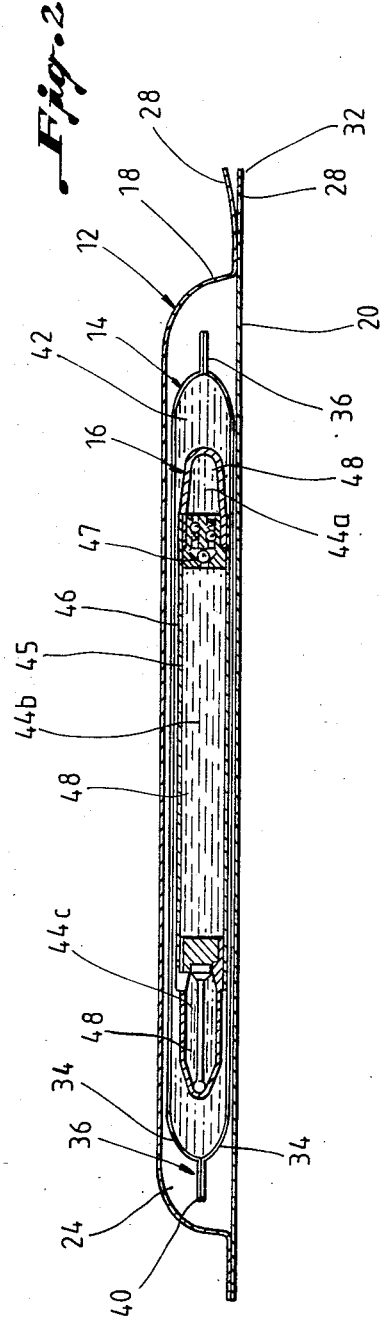

METHOD AND APPARATUS FOR PACKAGING A FLUID CONTAINING PROSTHESIS

BACKGROUND OF THE INVENTION

1. Field of the Invention

This invention relates generally to medical devices and particularly to prosthetic devices which may be surgically implanted in a sterile condition. More specifically, the present invention relates to methods and apparatus for packaging such devices.

2. Brief Description of Background Art

Currently a wide variety of prosthetic devices are available for surgical implantation. The technology is advancing so rapidly that it is now possible to almost equal or perhaps even improve upon the operation of various organs through the implantation of artificial, prosthetic devices. These prosthetic devices are often made of materials which are compatible with human tissue so that the prosthetic device does not cause rejection from its host. As a result, a number of implants have silicone outer layers because of silicone's ready tolerance by the body.

There are presently a number of commercially available penile prostheses. These devices are inserted in the corpus cavernosa of the penis to produce an erection in men who would otherwise be impotent. The so-called rigid rod penile prostheses continuously assume a rigid state. In addition, other devices have been developed which enable the simulation of an erection and thereafter selectively assume a relaxed, non-erect state. Such devices include malleable penile prostheses, which may include a bendable wire or the like and inflatable penile prostheses. The inflatable penile prostheses generally include at least two fluid reservoirs, one of which stores a fluid prior to an erection and the other of which stores fluid during erection. The configuration of the reservoirs is such that the device is flaccid in one condition and erect in another condition. The fluid may be drained back to the original reservoir so that the penis may assume a flaccid state after erection.

The inflatable penile prostheses therefore generally include at least one bladder or reservoir which is filled with a liquid or a gas. Conventionally, the bladder is filled with a physiological solution compatible with the body. In the past, inflatable penile prostheses have been shipped to the surgeon for implantation in a dry state. When the surgion received the penile implant and was ready to begin the surgical procedure, it was first necessary to fill the prosthesis with sterile physiological solution. This often meant that the surgeon must measure the required quantity of fluid and then pour or otherwise load the fluid into the relatively small and sometimes difficult to handle prosthesis. A considerable waste of valuable surgeon's time results. Moreover, the possiblility of an inadvertent error in the loading procedure was always present. The manufacturer was therefore at a loss to insure reliable operation in the face of the surgeon's intervention.

It was believed to be necessary to ship the prostheses in a dry state because of the permeability of silicone. Silicone and other permeable materials enable fluids to interchange between the interior of the device and the surrounding environment, as when the contained fluid migrates outwardly or air migrates inwardly through a wall. Migration through the wall could upset the fluid volume required to precisely simulate an erection in operation. For example, if the fluid migrated outwardly of the device by osmosis, the required fluid volume might not be available so that the device would not work adequately. Similarly, if air was allowed to migrate inwardly, air bubbles could be created which might also adversely affect the operation of the device.

Thus, the inventor of the present invention appreciated that it would be highly desirable to provide a method and apparatus which permits the transportation of a prosthetic device in a fluid filled state so that the necessity for loading the fluid into the prosthesis, for example in the operating room, is avoided.

SUMMARY OF THE INVENTION

The present invention provides a method and apparatus for packaging a fluid filled prosthetic device that overcomes the problem of fluid migration during shipment or storage. In one embodiment, the prosthetic device may be a penile prosthesis. The method and apparatus of the present invention is capable of being economically and practically implemented. Moreover, with the present invention a method and apparatus for packaging a prosthetic device is possible which insures that the volume and solute concentration of a fluid contained within such a device is preserved during shipping and storage. The present invention also enables implantation of devices containing fluids of predetermined solute concentrations.

The present invention may implement a method and apparatus for packaging that allows a prosthetic device to be delivered in a sterile condition. In certain embodiments the present invention permits visual detection of the loss of packaging integrity.

These and other aspects of the present invention may be achieved by a packaged fluid containing prosthesis adapted to be implanted in a sterile condition. The prosthesis includes a prosthetic device having a closed, permeable housing defining a fluid containing chamber. A sealed, substantially fluid impenetrable enclosure surrounds the housing and defines a fluid retaining space between the enclosure and the housing. The enclosure is adapted for separation from the device prior to implantation of the device. The enclosure contains a liquid in the space that is substantially in mass transfer equilibrium with the fluid in the chamber. The enclosure may in turn be surrounded by a wrapper which may be peeled away by a non-sterile nurse to expose the interior enclosure for handling by a sterile nurse.

In accordance with another embodiment of the present invention, a method for packaging a fluid containing prosthesis adapted to be implanted in a sterile condition includes the step of filling a chamber within a closable housing of the prosthesis, with fluid. The housing is then enclosed within a sealed substantially fluid impenetrable enclosure that surrounds the housing and defines a fluid retaining space between the enclosure and the housing. The enclosure is filled with a liquid with activities that substantially match the activities of the fluid within the chamber. Thereafter, the sealed, substantially fluid impenetrable enclosure may be enclosed within a package so that it may be handled for transport and opened by a non-sterile nurse. After the package is opened by a non-sterile nurse, a sterile nurse may grasp and open the sealed, substantially fluid impenetrable enclosure. The surgeon may then take the prosthesis, already in a filled state, for essentially immediate implantation.

In accordance with yet another embodiment of the present invention, a packaged fluid containing prosthesis adapted to be implanted in a sterile condition includes a prosthetic device. The device has a closed, permeable housing defining a fluid containing chamber such that a mass transfer gradient would exist across the housing once the housing is exposed to atmospheric conditions. A sealed, substantially fluid impenetrable enclosure surrounds the housing and defines a fluid retaining space between the enclosure and the housing. The enclosure is adapted for separation from the device prior to use of the device. The enclosure contains a fluid in the space with activities that substantially match the activities of the fluid in the chamber such that the mass transfer gradient across the permeable housing is insubstantial.

BRIEF DESCRIPTION OF THE DRAWINGS

FIG. 1 is a front elevational view of one embodiment of the present invention; and FIG. 2 is a cross-sectional view taken generally along the line 2—2 in FIG. 1, schematically showing a penile prosthesis.

DESCRIPTION OF A PREFERRED EMBODIMENT

Referring to the drawing wherein like reference characters are utilized for like parts throughout the several views, a package 10, shown in FIG. 1, is adapted to contain a sterile prosthetic device for implantation in humans or animals. The package 10 may be formed of an outer bag 12, a sealed, substantially fluid impenetrable enclosure 14 contained within the bag 12 and a prosthetic device 16, shown in FIG. 2, contained within the enclosure 14. As used herein the term "fluid" includes liquids or gases and the term "liquid" includes gels. The prosthetic device 16 is conveniently packaged at a manufacturing facility for subsequent transport and storage at a surgical facility. The interior of the outer bag 12 may define a sterile space suitable for contact by a sterile nurse in an operating room.

The outer bag 12 may be formed of a flexible upper sheet 18 and a flexible lower sheet 20. Conveniently the lower sheet 20 is formed of a non-woven fabric, such as Tyvek, paper or paper laminate material while the upper sheet 18 may be formed of a plastic, sealable film material that is transparent. If steam sterilization is intended, the lower sheet 20 must be breathable so that water vapor may penetrate during steam sterilization. The lower sheet 20 may be coated, on its surface that faces the upper sheet 18, with a heat sealable or pressure activated resin. Then the upper sheet 18 may be secured peripherally at the seams 22 to the lower sheet 20 by conventional techniques, including adhesive bonding techniques or heat bonding techniques. The sheets 18 and 20 are made of material that provides a barrier to micro-organisms. In any case, the two sheets 18 and 20 are sealed together along the seam 22 to define a microorganism excluding space 24 containing the sealed, fluid impenetrable enclosure 14. Advantageously, the seam 22 is a "peel open" seam, as is well known in the art.

The uppermost portion 26 of the seam 22 has a V-shaped configuration such that the "V" points outwardly. The portion 26 defines a pair of separable flaps 28 connected together at the corners 30 by heat seals or other conventional bonding techniques. A notch 32 in the lower sheet 20 permits easy separation of the flaps 28 with respect to one another.

As shown in FIG. 2, the enclosure 14 is contained within the bag 12. The enclosure 14 is advantageously formed of a laminated film structure which presents a very high barrier to the passage of fluids. For example, the enclosure 14 may be formed of a laminate of polyester, aluminum foil, and polypropylene films, for example, of the type used to withstand the temperature, pressure, and moisture conditions of a retort sterilization process. The enclosure 14, like the bag 12, may be formed of two relatively flexible sheets of material 34 peripherally seamed together along the line 36. By making at least the facing layers of the sheets 34 of heat sealable material, the sheets 34 may be bonded by heat sealing techniques. A weakening 38 is defined along the lower portion 40 of the seam line 36. The weakening 38, conveniently in the form of a slit or notch, extends partially through the seam line 36 to facilitate tear opening of the enclosure 14. Additional weakenings 38 may be provided as desired.

The prosthetic device 16 is contained within the enclosure 14 and is surrounded by a fluid medium 42. Advantageously, the fluid medium 42 fills the interior of the enclosure 14 so that it bulges discernably. For example, the enclosure 14 may bulge so that it assumes a relatively smooth elliptical cross-sectional configuration.

The prosthetic device 16 may be any device that includes at least one closed internal reservoir, indicated as 44 in FIG. 2, containing or excluding a fluid which is subject to fluid migration or mass transfer through the permeable prosthesis walls, indicated as 46 in FIG. 2, for example when the device 16 is exposed to atmospheric conditions. If the walls 46 are made of silicone, which is very often the case in prosthetic devices, an osmotic pressure gradient may exist across the walls 46 when the device 16 is exposed to certain conditions in transport or storage that would result in migration of the fluid through the walls 46. This migration may take the form of mass transfer outwardly of fluid 48 held within the reservoir 44 or the migration inwardly of fluid surrounding the prosthetic device 16. For example, fluid 48 in the form of liquid held within a reservoir 44 may be prone to migrate outwardly so that the volume of the liquid dissipates. Air or other ambient gas may be prone to migrate inwardly. However, mass transfer may result from a pressure, concentration, or electrical imbalance across the walls 46.

In the illustrated prosthetic device 16, an inflatable penile prosthesis, a group of three serially arranged reservoirs 44a, 44b, and 44c are capable of holding a physiological solution 48 and selectively communicating with one another. The physiological solution may be made up of, for example, 0.9% by weight sodium chloride in sterile water combined with a bacteriostatic agent, such as 0.94% by weight benzyl alcohol. Fluid contained in the rear tip reservoir 44c may be manually pumped to the front tip reservoir 44a by way of an axial passageway 45. The fluid then passes inwardly into the reservoir 44b. The pressure that builds up in the reservoir 44b causes the device 16 to become erect. When the valve 47 is manually actuated the fluid flows from the reservoir 44b to the reservoir 44c. The reservoir 44b then becomes flaccid, causing the entire device 16 to take a flaccid configuration.

In the case of a prosthetic device 16 designed to be used as a penile implant inserted within the corpus cavernosa of a penis, the mass transfer of fluid to or from the device 16, prior to implantation, could affect the operation of the device 16 due to the loss of liquid volume or the occurrence of air bubbles within the reservoir 44. However, while the present invention is described with respect to a penile prosthesis, the present invention is generally applicable to any prosthetic device which includes a fluid containing reservoir limited by a housing that permits a mass transfer gradient to exist across the housing when the housing is exposed to conditions that could result in migration of fluid through the housing. For example, the present invention may be useful in conjunction with breast augmenting implants and implantable drug delivering devices. The fluid within the reservoir 44 may take the form of either a liquid or a gas.

By making the activities of the fluid medium 42 match the activities of the fluid 48 within the reservoir 44, the mass transfer gradient may be reduced essentially to zero or to a small enough value that fluid migration is not a problem. The fluid pressure as well as the solute concentration may be balanced across the walls 46 in order to match the activities of the fluids on opposite sides of the walls 46.

When the fluid 48 within the reservoir 44 is a saline solution, as may be the case with inflatable penile prostheses, a liquid solution having a salt concentration substantially equal to that of the fluid 48 is utilized as the fluid medium 42. This effectively matches the osmolarity and activities across the walls 46 and results in the retention of the fluid within the reservoir 44, not only in terms of fluid volume, but also in view of fluid concentration of solute. Thus, in effect, where pressure is balanced, it is only necessary to balance the solute concentration between the fluid 48 and the fluid medium 42 in order to preserve the solute concentration of the fluid within the reservoir 44. However, when certain solute constituents do not contribute to the mass transfer gradient, it may not be necessary to balance them across the barrier. Regardless of the chemistry of the solute, the same result can be achieved. Thus, the present invention is not necessarily limited exclusively to the use of prosthetic devices which contain any particular solution within a reservoir 44.

It is also possible to attain mass transfer equilibrium without being in pressure or concentration or electrical equilibrium. This is because it is possible to balance an imbalance of one kind, e.g. a pressure imbalance, with an opposite imbalance of another kind, e.g. a concentration imbalance so that overall mass transfer equilibrium is achieved.

Moreover, it is of course possible with the present invention to engineer a prosthetic device that is in mass transfer imbalance with respect to body fluids. This could be the case, for example, with tissue expanders. Under these circumstances the prostetic device is packaged to attain a mass transfer equilibrium in shipping and storage for example, and yet, in use, the device is purposefully in activity imbalance with body fluids. Then the osmolality of the fluids 42, 48 may be different from that of body fluids so that a desired rate of controlled mass transfer to or from the prosthetic device may be attained. However, with a penile prosthesis, for example, it is advantageous that the device be engineered to attain mass transfer balance, in use, with respect to body fluids. Then the osmolality of the fluids 42, 48 may be substantially the same as that of body fluid.

The present invention has been illustrated with respect to a package 10 using a flexible enclosure 14 and bag 12 surrounding a relatively flexible prosthetic device 16, that is advantageous under many circumstances. The present invention is also applicable to the use of rigid or non-deformable enclosures 14, bags 12 and devices 16.

The present invention may be utilized in generally the following fashion. Initially, the prosthetic device 16 is manufactured in the conventional way except that the fluid 48 is immediately loaded into the reservoir 44 defined within the walls 46 of the device 16. Next, the fluid medium 42 is poured into the enclosure 14. The device 16 is then loaded into the partially sealed, fluid impenetrable enclosure 14 through a single open end thereof. The activities of the fluid medium 42 are designed to match the activities of the fluid 48 across the walls 46 of the prosthetic device 16 while eliminating air. In this way the volume and concentration of solute of the fluid 48 may be preserved during extended shipping and storage periods.

Thereafter, the open end of the enclosure 14 is sealed and the entire enclosure 14 may then be slid between the sheets 18 and 20 of the outer bag 12. The outer bag 12 is then sealed along the seams 22. At this point, the entire package 10 may be subjected to conventional sterilization techniques. For example, the package 10 may be exposed to high pressure steam in an autoclave sterilization process in order to sterilize the enclosure 14, the fluid medium 42 and the prosthetic device 16. After sterilization, the outer bag 12 may be touched by non-sterile personnel without affecting the sterility of the outer bag 12 contents.

The entire package 10 with the prosthetic device 16 enclosed in a fluid filled sate may then be shipped to a hospital or other surgical facility. After a period of storage, when it is time to implant the prosthetic device 16 within a patient, a non-sterile nurse grasps the package 10 and pulls open the outer bag 12. This may be accomplished by separating the sheets 18 and 20 using the notch 32 to part the flaps 28. With one flap 28 held in each hand, the non-sterile nurse can pull the flaps 28 apart breaking the corner seals 30 and propagating a peeling tear between the sheet 18 and 20 that begins along the upper portion 26 of the seam 22. Because of the essentially pointed configuration of the upper portion 26 of the seam 22, the initial tear at the point 50 immediately propagates rearwardly so that the two sheets 18 and 20 may be relatively easily separated in a peeling motion.

With the bag 12 opened, a sterile nurse, who has been prepared to meet operating room sterility standards, then grasps and removes the sterile enclosure 14 from the outer bag 12. When the surgeon is ready to begin the implantation, the sterile nurse opens the enclosure 14. This may be done by tearing the enclosure 14 along the weakening 38 so that the prosthetic device 16 is exposed for grasping by the surgeon. If the sterile nurse notices that the enclosure does not appear to be suitably filled, a new package 10 may be requested in order to avoid the possibility that the integrity of the enclosure 14 has not been preserved.

The surgeon may then remove the sterile prosthetic device 16 for immediate implantation. Since the fluid 48 has already been loaded into the reservoir 44, the surgeon does not have to fill the prosthetic device 16 during the operating procedure. The surgeon may be confident that the required volume of fluid 48 is contained within the prosthetic device 16 and that the concentration of the solute within the fluid 48 is inviolate. The manufacturer may also be more confident of the reliability of the device 16 through the ability to control the filling of the prosthesis 16.

While the invention has been described with respect to a single preferred embodiment, those skilled in the art will appreciate a number of variations and modifications thereof and it is intended within the appended claims to cover all such variations and modifications as come within the true spirit and scope of the present invention.

What is claimed is:

1. A packaged fluid containing prosthesis adapted to be implanted in a sterile condition, said prosthesis comprising:
    a prosthetic device having a closed, permeable housing defining a fluid containing chamber;
    a sealed, substantially fluid impenetrable enclosure surounding said housing and defining a liquid retaining space between said enclosure and said housing, said enclosure adapted for separation from said device prior to implantation of said device; and
    said enclosure containing a liquid in said space with activities that substantially match the activities of the fluid in said chamber such that the mass transfer gradient acoss the permeable housing is insubstantial.
2. The prosthesis of claim 1 wherein said prosthetic device is an inflatable penile prosthesis.
3. The prosthesis of claim 1 wherein the liquid in said space and the fluid in said chamber are both saline solutions of substantially the same salt concentrations.
4. The prosthesis of claim 1 wherein said fluid in said chamber is a liquid.
5. The prosthesis of claim 1 wherein said enclosure is itself enclosed within a container adapted to exclude micro-organisms.
6. The prosthesis of claim 5 wherein said container is a peel open bag.
7. The prosthesis of claim 1 wherein the fluid within said enclosure is filled sufficiently that it bulges discernably.
8. The prosthesis of claim 1 wherein said prosthetic device and said enclosure are sterilizable by autoclaving.
9. The prosthesis of claim 1 wherein said enclosure includes a weakening to facilitate tear opening.
10. The prosthesis of claim 9 wherein said enclosure is made of a laminate including aluminum foil and a heat sealable plastic sheet material.
11. The prosthesis of claim 1 wherein said enclosure is formed of flexible sheet material.
12. The prosthesis of claim 1 wherein the liquid in said space and the fluid in said chamber are of substantially the same osmolality as body fluids.
13. The prosthesis of claim 1 wherein the liquid in said space and the fluid in said chamber are of controlled osmolality different from that of body fluids.

14. A method of packaging a fluid containing prosthesis adapted to be implanted in a sterile condition, said method comprising the steps of:
    filling a closable permeable housing within a prosthetic device with a fluid;
    enclosing said prosthetic device within an enclosure which contains a liquid with activities that substantially match the activities of the fluid within the housing, thereby rendering insubstantial the mass transfer gradient across the permeable housing; and
    sealing said enclosure about said prosthetic device to define a sealed substantially fluid impenetrable barrier to fluid migration.
15. The method of claim 14 including the step of enclosing said enclosure within an outer bag.
16. The method of claim 15 including the step of opening said outer bag 12 in a nonsterile fashion while opening said enclosure in a sterile fashion to expose said prosthetic device.
17. The method of claim 16 including the step of peeling open said outer bag and said enclosure.
18. The method of claim 15 including the step of sterilizing said prosthetic device in a liquid filled state within said enclosure and said outer bag.
19. The method of claim 14 including the steps of filling said device with a solution and enclosing said prosthetic device within an enclosure filled with a solution having a solute concentration substantially equal to the solute concentration of the solution in said device.
20. The method of claim 14 including the step of enclosing said enclosure within a container that excludes micro-organisms.
21. A packaged fluid containing prosthesis adapted to be implanted in a sterile condition, said prosthesis comprising:
    a prosthetic device having a closed, permeable housing defining a fluid containing chamber, such that a mass transfer gradient would exist across said housing once said housing is exposed to atmospheric conditions;
    a sealed, substantially fluid impenetrable enclosure surrounding said housing and defining a fluid retaining space between said enclosure and said housing, said enclosure adapted for separation from said device prior to use of said device; and
    said enclosure containing a fluid in said space with activities that substantially match the activities of the fluid in said chamber such that the mass transfer gradient across the permeable housing is insubstantial.
22. The prosthesis of claim 21 wherein said prosthetic device is an inflatable penile prosthesis.
23. The prosthesis of claim 21 wherein the fluid in said space and the fluid in said chamber are both saline solutions of substantially the same salt concentrations.
24. The prosthesis of claim 21 wherein said fluid in said space and said fluid in said chamber are liquids.

* * * * *

UNITED STATES PATENT AND TRADEMARK OFFICE
CERTIFICATE OF CORRECTION

PATENT NO. : 4,597,765
DATED : July 1, 1986
INVENTOR(S) : William M. Klatt

It is certified that error appears in the above—identified patent and that said Letters Patent is hereby corrected as shown below:

Column 7, line 17 "surounding" should read "surrounding".

Column 7, line 24 "acoss" should read "across".

Signed and Sealed this
Fourteenth Day of October, 1986

[SEAL]

*Attest:*

DONALD J. QUIGG

*Attesting Officer*   *Commissioner of Patents and Trademarks*